United States Patent [19]

Yu et al.

[11] 4,067,975

[45] Jan. 10, 1978

[54] TREATMENT OF PSORIASIS WITH 6-AMINONICOTINAMIDE AND THIONICOTINAMIDE

[76] Inventors: Ruey J. Yu, 4400 Dexter St., Philadelphia, Pa. 19128; Eugene J. Van Scott, 1138 Sewell Lane, Rydal, Pa. 19046

[21] Appl. No.: 601,411

[22] Filed: Aug. 4, 1975

[51] Int. Cl.$^2$ .................... A61K 31/455; A61K 31/57
[52] U.S. Cl. .................................... 424/240; 424/168; 424/172; 424/250; 424/266
[58] Field of Search ........................ 424/266, 250, 240

[56] References Cited

U.S. PATENT DOCUMENTS

| | | | |
|---|---|---|---|
| 2,199,839 | 5/1940 | Renshaw et al. | 424/266 |
| 2,791,534 | 5/1957 | Schaaf et al. | 424/266 |
| 3,148,115 | 9/1964 | Johnson et al. | 424/266 |
| 3,337,570 | 8/1967 | Sherlock et al. | 424/266 |
| 3,415,835 | 12/1968 | Stempel et al. | 424/266 |

OTHER PUBLICATIONS

Zackheim, Arch Dermatol, vol. 111, July 1975, pp. 880–882.

*Primary Examiner*—Albert T. Meyers
*Assistant Examiner*—Vera C. Clarke
*Attorney, Agent, or Firm*—LeBlanc & Shur

[57] ABSTRACT

A treatment to alleviate the symptoms of psoriasis consisting of topical application of a cream, ointment or lotion containing as an active ingredient one or more of the following compounds: 6-aminonicotinamide, 6-carbamoylnicotinamide, 6-chloronicotinamide, 6-dimethylaminonicotinamide, 6-formylaminonicotinamide, 6-aminonicotinic acid, 6-aminonicotinic acid methyl ester, 6-hydroxy nicotinic acid, thionicotinamide, 2-aminopyrazinamide and 2-carbamoylpyrazinamide is disclosed. The therapeutic composition may include a single member of the above listed active ingredients present in a total amount of from 0.01 to 5 percent by weight of the total composition, or a plurality thereof present in a preferred concentration range of from 0.01 to 2 percent by weight of the total composition. Topical application of the therapeutic composition in a cream, ointment, or a water or alcohol solution has been found to achieve from substantial to complete remissions of psoriasis in humans.

38 Claims, No Drawings

TREATMENT OF PSORIASIS WITH 6-AMINONICOTINAMIDE AND THIONICOTINAMIDE

This invention relates to a treatment for psoriasis and specifically to a composition containing one or more compounds which have been found to be effective when topically applied, to improve and heal the skin lesions of psoriasis in humans.

Psoriasis is a chronic disease, and remains a disfiguring and disabling cutaneous impairment to millions of persons. Its etiology is completely unknown, and therefore, prevention remains inconceivable. Therapy has necessarily been empiric, and has included the systemic use of antimitotic drugs such as methotrexate to induce remissions of the lesions. However, acute and chronic toxicity on tissues other than skin has discredited use of methotrexate. Therefore it is imperative that other means of therapy be found by external delivery of drugs so that toxicity is confined chiefly to the skin, or by the discovery of new drugs having nontoxic attributes.

In our prior patent application entitled TREATMENT OF PSORIASIS, Ser. No. 371,516, filed June 19, 1973, now U.S. Pat. No. 3,904,766, we described and claimed the use of mechlorethamine hydrochloride ointment in the treatment of psoriasis by topical application. We also described that in an oil base the compound formed a stable composition.

Prior to our above invention mechlorethamine hydrochloride, a nitrogen mustard, had been generally discounted as a treatment for psoriasis because, in effective dosages a high percentage of patients became sensitized. In addition, the compound proved to be highly unstable in an aqueous solution and rapidly degraded to what was considered an ineffective byproduct by those skilled in the art.

The treatment described in our above application, however, was necessarily proceeded by inducing an immunological tolerance so that the patient would not be susceptible to a delayed hypersensitive reaction. The procedure for inducing immune tolerance included weekly intraveneous injections of 0.2 milligrams of mechlorethamine hydrochloride in an aqueous solution over at least a three week period prior to initiation of topical therapy.

In our prior patent application Ser. No. 455,665, filed Mar. 28, 1974, now U.S. Pat. No. 3,920,840, we described and claimed our discovery that psoriatic conditions could be successfully treated by utilizing one of the degradation products of mechlorethamine hydrochloride, N-methyldiethanolamine, a compound which is not primarily either antimitotic nor allergic. This compound was found to be essentially nontoxic to both animals and humans when used as a topical agent in a therapeutic composition containing from 0.5 to 5 percent by weight thereof. The compound also caused no detectable signs of any irritation to human skin.

It has now been discovered that psoriatic conditions may also be successfully treated by utilizing an entirely different class of compounds which also are primarily neither antimitotic nor allergic. Therefore, it is also unnecessary to induce an immune tolerance prior to topical therapy with the compounds of this invention. The present invention includes topical treatment of psoriatic lesions with one or more 6-substituted nicotinamides, 6-substituted nicotinic acid and esters thereof, or 2-substituted pyrazinamide or thionicotinamide.

It should be emphasized, however, that of the above classes the following compounds were found to be highly effective: 6-aminonicotinamide, 6-carbamoylnicotinamide 6-chloronicotinamide, 6-dimethylaminonicotinamide, 6-formylaminonicotinamide, 6-aminonicotinic acid, 6-aminonicotinic acid methyl ester, 6-hydroxy nicotinic acid, thionicotinamide, 2-aminopyrazinamide, and 2-carbamoylpyrazinamide. While other compounds within the aforementioned classes may be effective, it was found that nicotinamide, nicotinic acid, isoniazid, and 2-aminonicotinic acid were totally ineffective in causing remissions of psoriatic conditions.

It has been established then through extensive tests on humans having psoriasis that topical application of either an alcohol or water solution or an ointment or lotion containing from 0.01 to 5 percent of certain members of the following groups of compounds, or their analogs are effective to cause remissions of psoriatic conditions. The groups of compounds as noted above are 6-substituted nicotinamides, 2-substituted pyrazinamides, or their analogs. Although the above named compounds were found to be effective when present in from 0.01 to 5 percent by weight of the total therapeutic composition, the preferred concentration range is from 0.01 to 2 percent thereof. The therapeutic compositions of this invention were found to be effective, when applied on a daily basis, to cause within about 1-3 weeks time a return of the affected skin areas to a normal skin condition.

Accordingly, it is an object of this invention to provide a relatively nontoxic, nonallergenic medicinal composition which, when topically applied, will reliably alleviate the symptoms of psoriasis.

It is another object to provide a medicinal composition containing at least one 6-substituted nicotinamide, 6-substituted nicotinic acid and esters thereof, 2-carbamoylpyrazinamide, 2-aminopyrazinamide, or thionicotinamide which, when topically applied, will alleviate the symptoms of psoriasis.

It is another object of this invention to provide a method for treating psoriasis with relatively nontoxic ointment or solution of water or alcohol containing a 6-aminonicotinamide or its analogs or 2-carbamoylpyrazinamide or its analogs or thionicotinamide.

It is still another object to provide a safe and efficient method for treating the symptoms of psoriasis through regular topical application of a medicinal composition which will promote healing within about 1-3 weeks.

It is yet another object of this invention to provide a safe and efficient method for treating the symptoms of psoriasis through regular topical application of a medicinal composition containing from about 0.01 to 5 percent of at least one member selected from the group consisting of 6-substituted nicotinamides; 6-aminonicotinamide 6-carbamoylnicotinamide, 6-chloronicotinamide, 6-dimethylaminonicotinamide, and 6-formylaminonicotinamide; 6-substituted nicotinic acids, 6-amino nicotinic acid, 6-aminonicotinic acid methyl ester, and 6-hydroxynicotinic acid; the 2-substituted pyrazinamides, 2-carbamoylpyrazinamide, and 2-amino pyrazinamide; and thionicotinamide.

PREPARATION OF THE THERAPEUTIC COMPOSITIONS

In order to prepare the compositions of this invention at least one of the aforementioned compounds is initially dissolved in a solvent such as water, 1N HCl, ethanol, or acetone. The solution thus prepared may then be admixed in a conventional manner with commonly available ointment bases such as hydrophilic ointment (USP) or petrolatum (USP). The concentration of the compound ranges from 0.01 to 5.0 percent by weight of the total composition. The preferred concentration range, however, is from 0.01 to about 2 percent.

If desired, two or more of aforementioned compounds may be admixed as described above to form a composition of this invention. In this instance it is preferred that the concentration of the compounds not exceed about 2 percent by weight of the total composition.

In addition, the therapeutic composition of this invention may include one or more steroid compounds such as hydrocortisone or its acetate derivative incorporated in the ointment as described above. The steroid may function against any irritating action with highly sensitive skin, or may be effective against unrelated or remotely related disease conditions. If a steroid is added as an additional ingredient, it is preferred that the concentration of this compound also not exceed 2 percent by weight of the total composition.

The water, HCl, ethanol, or acetone solvent used to initially dissolve the compound of this invention may have a concentration of from 1 to 20 percent by volume of the total composition. The preferred concentration thereof, however, is about 10 percent by volume of the total composition.

The therapeutic ointments of this invention, prepared as described above, may be stored in ointment jars at room temperature for extended periods of time. No change in clinical effectiveness due to prolonged periods of storage has been observed.

The compounds of this invention may also be utilized in a solution or lotion form. A typical solution utilizing the compounds of this invention comprises at least one of the above named compounds dissolved directly in a mixture of water, ethanol, and propylene glycol in a volume ratio of preferably 40:40:20, respectively. The pH of the solution should then be adjusted to between 4 and 5 with 1N HCl.

The ratio of each component of a lotion of this invention, however, may vary, but the preferred concentrations of ethanol and propylene glycol should not exceed 70 percent and 30 percent, respectively. When solutions are formulated according to this invention the compound concentration may also be from 0.01 to 5 percent by weight, but a concentration of from 0.01 to 2 percent is preferred. One or more compounds may be admixed in a solution of this invention, and it is preferred that the total concentration of the mixture not exceed about 2 percent by weight.

In an alternative way of preparing the therapeutic compositions, one of the aforementioned compounds of the present invention may also be directly incorporated into the composition without utilized a solvent for dissolution.

The following Examples are illustrative of formulations of compositions according to this invention. Although the Examples utilize a named compound, the Examples are not intended to be limited to the specific compound named, but any member of the above described group of compounds or combination thereof could be substituted therefor within the scope of this invention.

EXAMPLE 1

A 6-aminonicotinamide 0.1 percent ointment may be prepared as follows:

6-Aminonicotinamide, 0.1 g, is dissolved in 3.6 ml of 0.2 N HCl and 6.3 ml water. The solution thus obtained is admixed with commercially available USP grade hydrophilic ointment (90g) to a uniform consistency. The ointment thus prepared is stored preferably in opaque jars at room temperature.

EXAMPLE 2

6-Formylaminonicotinamide 0.1 percent ointment may be prepared as follows:

6-Formylaminonicotinamide 0.1 g is dissolved in 5 ml of water and 4.9 ml of ethanol. The solution is admixed with hydrophilic ointment USP grade (90 g) to a uniform consistency. This ointment also may be stored in opaque jars at room temperature.

EXAMPLE 3

A 6-aminonicotinic acid methyl ester 1 percent ointment may be prepared as follows:

6-Aminonicotinic acid methyl ester, 1 g, is dissolved in anhydrous ethanol (9 ml) and the solution is admixed with white petrolatum USP grade (54 g) and liquid petrolatum USP grade (36 g) to a uniform consistency. This ointment also may be stored in opaque jars at room temperature.

EXAMPLE 4

A 6-aminonicotinic acid 1 percent ointment is prepared as follows:

6-Aminonicotinic acid 1 g is dissolved in 7 ml of 1N HCl and 2 ml of water. The solution is admixed with USP grade hydrophilic ointment (90 g) to a uniform consistency. The ointment thus prepared is also stored in opaque jars at room temperature.

EXAMPLE 5

A 2-carbamoylpyrazinamide 1 percent ointment is prepared as follows:

2-Carbamoylpyrazinamide, also known as 2, 3-pyrazinedicarboxamide, 1g is dissolved in 5 ml of water and 4 ml of acetone. The solution is admixed with USP grade hydrophilic ointment (90 g) to a uniform consistency. The ointment thus prepared is also stored in opaque jars at room temperature.

EXAMPLE 6

A combination of two active ingredients in an ointment of this invention is prepared as follows:

6-Aminonicotinamide 0.1 g and thionicotinamide 0.5 g are dissolved in 3.6 ml of 0.2 N HCl and 5.8 ml of water. The solution is admixed with USP grade hydrophilic ointment (90 g) to a uniform consistency. This yellowish ointment may also be stored in opaque jars at room temperature.

EXAMPLE 7

An additional agent active against unrelated or remotely related conditions, such as niacin, may be combined with the active ingredient of this invention in an ointment composition without blocking the effectiveness of the active ingredient of this invention. The ointment may be prepared as follows:

6-Aminonicotinamide 0.1 g and nicotinic acid 0.2 g are dissolved in 3.6 ml of 0.1 N HCl and 6.1 ml water.

This solution is admixed with USP grade hydrophilic ointment (90 g) to a uniform consistency. This ointment also may be stored in opaque jars at room temperature.

EXAMPLE 8

A 6-aminonicotinamide 0.2 percent lotion is prepared as follows:

6-Aminonicotinamide 0.2 g is dissolved in 7.2 ml of 0.2 N HCl and the solution is admixed with 92.6 g of a water-in-oil lotion prepared from mineral oil, cottonseed oil, isopropyl palmitate and water with a surfactant such as sorbitan sesquioleate. The ingredients in said water-in-oil lotion are present for example in 10:10:5:70:5 parts by weight respectively. The lotion thus prepared is stored in a plastic squeeze bottle having a nozzle attached thereto. The lotion is suitable for use in an area such as the scalp.

EXAMPLE 9

A combination ointment containing a compound of this invention and a steroid active against any possible irritating effects thereof may be prepared as follows:

6-Aminonicotinamide 0.2 g is dissolved in 7.2 ml of 0.2 N HCl. This solution and hydrocortisone, USP, 0.2 g are admixed with 92.4 g of water-in-oil ointment prepared from mineral oil, white petrolatum, spermaceti, lanolin and water with a surfactant such as sorbitan sesquioleate. The ingredients of said water-in-oil ointment are present in 10:10:8:2:60:6 parts by weight, respectively. The ointment thus prepared is stored in opaque jars at room temperature.

EXAMPLE 10

A formulation without using any solvent for dissolution may be prepared as follows:

6-Aminonicotinamide crystals are converted to a powder form (200-400 mesh) with a ball-mill machine. Powdered 6-aminonicotinamide 0.5 g is directly admixed with 99.5 g of water-in-oil ointment prepared from mineral oil, white petrolatum, spermaceti and water with a surfactant such as sorbitan sesquioleate. The ingredients of said water-in-oil ointment are present in 10:10:6:68:6 parts by weight, respectively. The ointment thus prepared is stored in opaque jars at room temperature.

TEST RESULTS

In order to evaluate the compounds of this invention a total of more than 30 patients having psoriasis were treated with the composition as follows:

Patients with psoriasis were instructed to apply a thin film of an ointment formulated according to the above Examples to the lesions. Twice daily topical application was continued for several weeks. Generally, the affected skin became less scaly and less erythematous after 1 week of topical treatment. The scaly and erythematous lesions ordinarily were substantially restored to normal appearing skin after 2 weeks of treatment. The sites of the lesions, devoid of any scales and erythema, usually reached an improved state comparable to normal skin within 2 to 4 weeks after initial treatment.

Once normal appearing skin was restored it remained improved for one to several weeks, varying from patient to patient, without further application of the ointment. It is, however, necessary to continue the application of the ointment in order to maintain the skin free from recurrence of the overt disease.

In each of the tests, the compositions utilized were formulated according to the above representative Examples and contained compounds of this invention present in a total concentration of from 0.01 to 1 percent, by weight.

| Compound | No. of Patients | Therapeutic Effectiveness |
|---|---|---|
| 1. 6-Aminonicotinamide | 30 | 4+ |
| 2. 6-Carbamoylnicotinamide | 2 | 4+ |
| 3. 6-Chloronicotinamide | 2 | 3+ |
| 4. 6-Dimethylaminonicotinamide | 2 | 3+ |
| 5. 6-Formylaminonicotinamide | 2 | 4+ |
| 6. 6-Aminonicotinic Acid | 2 | 4+ |
| 7. 6-Aminonicotinic Acid Methyl Ester | 2 | 4+ |
| 8. 6-Hydroxynicotinic Acid | 3 | 4+ |
| 9. 2-Aminopyrazinamide | 2 | 4+ |
| 10. 2-Carbamoylpyrazinamide | 4 | 4+ |
| 11. Thionicotinamide | 2 | 4+ |
| 12. 6-Aminonicotinamide and Nicotinic Acid | 3 | 4+ |

3+ Disappearance of scale from lesions
4+ Restoration to normal looking skin

As shown by the above Table, nine compounds and one combination thereof achieved a 4+ result, restoring normal looking skin in all patients tested. The rest of the compounds achieved at least a 3+ result and achieved a restoration of normal textured skin in that the lesions were still only erythematous. The method of application utilized herein generally required twice daily topical applications, and the scaly lesions ordinarily were substantially cleared after about 2 weeks of treatment.

As noted above, use of the compositions of this invention, however, do not result in a permanent cure. It has been observed that when regular application of a composition of this invention is terminated, normal appearing skin will remain for varying periods of time from a week to several weeks depending upon the patient. However, when regular application is resumed the lesions again disappear and normal appearing skin is restored.

In summary, this invention includes the discovery of relatively nontoxic compositions which are neither antimitotic nor allergic and which are useful for alleviating the symptoms of psoriasis. The compositions may either be an ointment, a cream, or a water or alcohol solution of one or more of 6-substituted nicotinamides, 6-substituted nicotinic acids and esters thereof, or 2-substituted pyrazinamide or thionicotinamide. Specifically, the active compounds of this invention are 6-aminonicotinamide, 6-carbamoylnicotinamide, 6-chloronicotinamide, 6-dimethylaminonicotinamide, 6-formylaminonicotinamide, 6-aminonicotinic acid, 6-aminonicotinic acid methyl ester, 6-hydroxy nicotinic acid, thionicotinamide, 2-aminopyrazinamide and 2-carbamoylpyrazinamide. One or more of these compounds is present in the vehicle, either ointment, cream, or water or alcohol solution, in a total concentration of from 0.01 to 5 percent by weight. The composition of this invention may, if desired, also include a steroid such as hydrocortisone or its acetate. If a steroid is utilized the total concentrations of the compounds preferably would not exceed about 2 percent by weight. Furthermore, if desired, nicotinic acid may also be incorporated in a composition of this invention. If so, the total concentration of the active ingredient and nicotinic acid should not exceed about 2 percent by weight of the total composition.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A method for alleviating the symptoms of psoriasis in a human suffering therefrom comprising:
    applying, topically, to involved areas of the human body an effective amount of a composition of 6-aminonicotinamide in a concentration of from 0.01 to 5 percent by weight of the total composition, in a pharmaceutically acceptable carrier.

2. The method of claim 1 wherein 6-aminonicotinamide is present in a concentration of from 0.01 to about 2 percent.

3. The method of claim 1 wherein said carrier comprises a member selected from the group consisting of water, ethanol, and acetone.

4. The method of claim 1 wherein said carrier comprises a member selected from the group consisting of hydrophilic ointment and petrolatum.

5. A therapeutic composition for alleviating the symptoms of psoriasis in a human by topical application to involved areas of the human body comprising:
    6-aminonicotinamide present in a concentration of from 0.01 to 5 percent, by weight, of the total composition in a pharmaceutically acceptable carrier.

6. The composition of claim 5 wherein 6-aminonicotinamide is present in a concentration of 0.01 to about 2 percent by weight of the total composition.

7. The composition of claim 5 further comprising a member selected from the group consisting of water, hydrochloric acid, ethanol, and acetone, said member present in a concentration of from 1 to 20 percent by volume of the total composition.

8. The composition of claim 7 wherein said member is present in a concentration of about 10 percent by volume.

9. The composition of claim 5 wherein said carrier is selected from the group consisting of petrolatum and hydrophilic ointment.

10. The composition of claim 5 wherein said carrier comprises a mixture of a liquid and an ointment base, said liquid comprising 3.6 parts of a 0.2N HCl solution and 6.3 parts water, by volume, admixed with said ointment base, said liquid and ointment base being present in said composition in a volume-weight ratio of 9.9 mls to 90 grams.

11. The composition of claim 5 wherein said carrier comprises a mixture of a liquid and an ointment base, said liquid comprising 5 parts water and 4.9 parts ethanol, by volume, admixed with said ointment base, said liquid and ointment base being present in said composition in a volume-weight ratio of 9.9 mls to 90 grams.

12. The composition of claim 5 wherein said carrier comprises a mixture of anhydrous ethanol and petrolatum, said ethanol and petrolatum being present in said composition in a volume-weight ratio of 9 mls to 90 grams.

13. The composition of claim 5 wherein said carrier comprises a mixture of a liquid and an ointment base, said liquid comprising 7 parts of a 1N HCl solution and 2 parts water, by volume, admixed with said ointment base, said liquid and ointment base being present in said composition in a volume-weight ratio of 9 mls to 90 grams.

14. The composition of claim 5 wherein said carrier comprises a mixture of a liquid and an ointment base, said liquid comprising 5 parts water and 4 parts acetone, by volume, admixed with said ointment base, said liquid and ointment base being present in said composition in a volume-weight ratio of 9 mls to 90 grams.

15. The composition of claim 5 wherein said carrier comprises a mixture of a liquid and an ointment base, said liquid comprising 3.6 parts of a 0.2N HCl solution and 5.8 parts water, by volume, admixed with said ointment base, said liquid and ointment base being present in said composition in a volume-weight ratio of 9.4 mls to 90 grams.

16. The composition of claim 5 wherein said carrier comprises a mixture of a liquid and an ointment base, said liquid comprising 3.6 parts of a 0.2N HCl solution and 6.1 parts water, by volume, admixed with said ointment base, said liquid and ointment base being present in said composition in a volume-weight ratio of 9.7 mls to 90 grams.

17. The composition of claim 5 wherein said carrier comprises a mixture of a liquid and a water-in-oil lotion, said liquid comprising 7.2 parts of a 0.2N HCl solution, by volume, and said water-in-oil lotion comprises 10 parts mineral oil, 10 parts cottonseed oil, 5 parts isopropyl palmitate, 70 parts water, and 5 parts sorbitan sequioleate, by weight, said solvent and lotion being present in said composition in a volume-weight ratio of 7.2 mls to 92.6 grams.

18. The composition of claim 5 further comprising, as an additional ingredient of said composition, about 0.2 parts by weight hydrocortisone.

19. The composition of claim 18 wherein said carrier comprises a mixture of a liquid and a water-in-oil ointment, said liquid comprising 7.2 parts of a 0.2N HCl solution, by volume, said water-in-oil ointment comprising 10 parts mineral oil, 10 parts white petrolatum, 8 parts spermaceti, 2 parts lanolin, 60 parts water, and 6 parts sorbitan sequioleate, by weight, said solvent and ointment being present in said composition in a volume-weight ratio of 7.2 mls to 92.4 grams.

20. A method for alleviating the symptoms of psoriasis in a human suffering therefrom comprising:
    applying, topically, to involved areas of the human body an effective amount of a composition of thionicotinamide in a concentration of from 0.01 to 5 percent by weight of the total composition, in a pharmaceutically acceptable carrier.

21. The method of claim 20 wherein thionicotinamide is present in a concentration of from 0.01 to about 2 percent.

22. The method of claim 20 wherein said carrier comprises a member selected from the group consisting of water, ethanol and acetone.

23. The method of claim 20 wherein said carrier comprises a member selected from the group consisting of hydrophilic ointment and petrolatum.

24. A therapeutic composition for alleviating the symptoms of psoriasis in a human by topical application to involved areas of the human body comprising:
    thionicotinamide present in a concentration of from 0.01 to 5 percent, by weight, of the total composition in a pharmaceutically acceptable carrier.

25. The composition of claim 24 wherein thionicotinamide is present in a concentration of 0.01 to about 2 percent by weight of the total composition.

26. The composition of claim 24 further comprising a member selected from the group consisting of water, hydrochloric acid, ethanol, and acetone, said member present in a concentration of from 1 to 20 percent by volume of the toal composition.

27. The composition of claim 24 wherein said member is present in a concentration of about 10 percent by volume.

28. The composition of claim 24 wherein said carrier is selected from the group consisting of petrolatum and hydrophilic ointment.

29. The composition of claim 24 wherein said carrier comprises a mixture of a liquid and an ointment base, said liquid comprising 3.6 parts of a 0.2N HCl solution and 6.3 parts water, by volume, admixed with said ointment base, said liquid and ointment base being present in said composition in a volume-weight ratio of 9.9 mls to 90 grams.

30. The composition of claim 24 wherein said carrier comprises a mixture of a liquid and an ointment base, said liquid comprising 5 parts water and 4.9 parts ethanol, by volume, admixed with said ointment base, said liquid and ointment base being present in said composition in a volume-weight ratio of 9.9 mls to 90 grams.

31. The composition of claim 24 wherein said carrier comprises a mixture of anhydrous ethanol and petrolatum, said ethanol and petrolatum being present in said composition in a volume-weight ratio of 9 mls to 90 grams.

32. The composition of claim 24 wherein said carrier comprises a mixture of a liquid and an ointment base, said liquid comprising 7 parts of a 1N HCl solution and 2 parts water, by volume, admixed with said ointment base, said liquid and ointment base being present in said composition in a volume-weight ratio of 9 mls to 90 grams.

33. The composition of claim 24 wherein said carrier comprises a mixture of a liquid and an ointment base, said liquid comprising 5 parts water and 4 parts acetone, by volume, admixed with said ointment base, said liquid and ointment base being present in said composition in a volume-weight ratio of 9 mls to 90 grams.

34. The composition of claim 24 wherein said carrier comprises a mixture of a liquid and an ointment base, said liquid comprising 3.6 parts of a 0.2N HCl solution and 5.8 parts water, by volume, admixed with said ointment base, said liquid and ointment base being present in said composition in a volume-weight ratio of 9.4 mls to 90 grams.

35. The composition of claim 24 wherein said carrier comprises a mixture of a liquid and an ointment base, said liquid comprising 3.6 parts of a 0.2N HCl solution and 6.1 parts water, by volume, admixed with said ointment base, said liquid and ointment base being present in said composition in a volume-weight ratio of 9.7 mls to 90 grams.

36. The composition of claim 24 wherein said carrier comprises a mixture of a liquid and water-in-oil lotion, said liquid comprising 7.2 parts of a 0.2N HCl solution, by volume, and said water-in-oil lotion comprises 10 parts mineral oil, 10 parts cottonseed oil, 5 parts isopropyl palmitate, 70 parts water, and 5 parts sorbitan sesquioleate, by weight, said solvent and lotion being present in said composition in a volume-weight ratio of 7.2 mls to 92.6 grams.

37. The composition of claim 24 further comprising, as an additional ingredient of said composition, about 0.2 parts by weight hydrocortisone.

38. The composition of claim 37 wherein said carrier comprises a mixture of a liquid and a water-in-oil ointment, said liquid comprising 7.2 parts of a 0.2N HCl solution, by volume, said water-in-oil ointment comprising 10 parts mineral oil, 10 parts white petrolatum, 8 parts spermaceti, 2 parts lanolin, 60 parts water, and 6 parts sorbitan sequioleate, by weight, said solvent and ointment being present in said composition in a volume-weight ratio of 7.2 mls to 92.4 grams.

* * * * *